(12) United States Patent
McAlister (10) Patent No.: US 8,623,925 B2
(45) Date of Patent: Jan. 7, 2014

(54) SYSTEM AND METHOD FOR PREPARING LIQUID FUELS

(75) Inventor: Roy E. McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

(21) Appl. No.: 13/315,226

(22) Filed: Dec. 8, 2011

(65) Prior Publication Data

US 2012/0149786 A1 Jun. 14, 2012

Related U.S. Application Data (60) Provisional application No. 61/421,189, filed on Dec. 8, 2010.

(51) Int. Cl.
*C07C 27/00* (2006.01)

(52) U.S. Cl.
USPC .......... 518/700; 518/702; 518/703; 518/704; 518/705; 518/728

(58) Field of Classification Search
USPC ......................................... 518/700–705, 728
See application file for complete search history.

(56) References Cited

U.S. PATENT DOCUMENTS

| | | | |
|---|---|---|---|
| 4,367,206 A | 1/1983 | Pinto | |
| 4,424,118 A | 1/1984 | Rankel | |
| 4,906,302 A | 3/1990 | Bruya | |
| 5,059,303 A | 10/1991 | Taylor et al. | |
| 6,180,396 B1 | 1/2001 | Ono | |
| 6,673,742 B2 | 1/2004 | Abdo et al. | |
| 8,070,835 B2 | 12/2011 | McAlister | |
| 2003/0062270 A1 | 4/2003 | McAlister | |
| 2003/0196810 A1* | 10/2003 | Vinegar et al. | 166/300 |
| 2007/0137246 A1 | 6/2007 | McKellar et al. | |
| 2007/0298478 A1 | 12/2007 | Offerman et al. | |
| 2009/0286890 A1* | 11/2009 | Joshi et al. | 518/701 |
| 2009/0289227 A1 | 11/2009 | Rising | |
| 2009/0318572 A1 | 12/2009 | Sakai et al. | |

FOREIGN PATENT DOCUMENTS

| | | |
|---|---|---|
| CN | 1918068 | 2/2007 |
| CN | 101448979 | 6/2009 |
| EP | 1002767 | 5/2000 |
| EP | 1219585 | 7/2002 |

(Continued)

OTHER PUBLICATIONS

Dolan, Eric. "Device uses sunlight to make liquid fuel". *The Raw Story*. Published: Dec. 24, 2010. 3 pages.

(Continued)

*Primary Examiner* — Jafar Parsa
(74) *Attorney, Agent, or Firm* — Perkins Coie LLP (57) ABSTRACT

Techniques, methods and systems for preparation liquid fuels from hydrocarbon and carbon dioxide are disclosed. The present invention can transform hydrocarbon and carbon dioxide generated from organic feed stocks or other industrial emissions into renewable engineered liquid fuels and store them in a cost-efficient way. The method of the present invention includes: supplying hydrocarbon and carbon dioxide to a heated area of a reaction chamber in controlled volumes; forming carbon monoxide by the energy provided by the heated area; transporting carbon monoxide and hydrogen to an reactor in controlled volumes; supplying additional hydrogen to the reactor; regulating the pressure in the reactor by adjusting the controlled volumes in order to achieve a predetermined object; forming the liquid fuel in the reactor according to the predetermined object; and, storing the liquid fuel in a storage device.

24 Claims, 5 Drawing Sheets

(56) References Cited

FOREIGN PATENT DOCUMENTS

| GB | 2086416 A | 5/1982 |
|---|---|---|
| JP | 2000-140621 A | 5/2000 |
| JP | 2002-193858 A | 7/2002 |
| JP | 2003-510403 | 3/2003 |
| JP | 2005-075925 | 3/2005 |
| JP | 2005-289856 | 10/2005 |
| JP | 2008-537956 | 10/2008 |
| JP | 2009-242248 | 10/2009 |
| WO | WO-2004-092055 | 10/2004 |
| WO | WO-2005-033250 | 4/2005 |
| WO | WO-2010078035 A2 | 7/2010 |

OTHER PUBLICATIONS

Lee et al. "Biological Hydrogen Production: Prospects and Challenges". *Trends in Biotechnology* 28.5. Jan. 2010. 10 pages.

Deluga et al. "AviationBioguels: Hydrotreated Renewable Jet," General Electric. Presentation Dated: Feb. 23, 2010. 13 pages.

International Search Report and Written Opinion for Application No. PCT/US2011/024799 Applicant: McAlister Technologies, LLC; Date of Mailing: Oct. 18, 2011 (9 pages).

International Search Report and Written Opinion for Application No. PCT/US2011/24812 Applicant: McAlister Technologies, LLC; Date of Mailing: Oct. 26, 2011 (12 pages).

Lopez et al., "Performance of the Southern California Edison Company Stirling Dish," Contractor Report, Prepared by Sandia National Laboratories Albuquerque, New Mexico, California, Printed Oct. 1993, 213 pages.

International Search Report and Written Opinion for Application No. PCT/US2011/064034 Applicant: McAlister Technologies, LLC; Date of Mailing Jan. 28, 2013 (9 pages).

\* cited by examiner

SYSTEM AND METHOD FOR PREPARING LIQUID FUELS

CLAIM OF PRIORITY

The present application claims priority to and the benefit of U.S. Patent Application No. 61/421,189, filed on Dec. 8, 2010 and titled LIQUID FUELS FROM HYDROGEN, OXIDES OF CARBON, AND/OR NITROGEN; AND PRODUCTION OF CARBON FOR MANUFACTURING DURABLE GOODS. The above-mentioned application is incorporated herein by reference in its entirety. To the extent the foregoing application and/or any other materials incorporated herein by reference conflict with the disclosure presented herein, the disclosure herein controls.

BACKGROUND

This application relates to techniques, methods, and systems related to preparation of liquid fuels from hydrocarbon and carbon dioxide generated from organic feed stocks or other industrial emissions.

Anaerobic digestion of organic substances generally produces hydrocarbon, such as methane, and carbon dioxide. Based on scientific research, methane and carbon dioxide are both green house gases that may cause global warming. It is advantageous to find a way to transform these gases into usable engineered fuels because this not only enhances the energy efficiency but also alleviates the global warming problem. For example, the ethanol production plants generate a considerable amount of carbon dioxide emission through their fermentation process. There is a pressing need to find useful applications of such carbon dioxide because it represents a large energy investment to grow and transport the grain or other fermented feedstock. Similarly it is important to provide practical ways to reduce their carbon dioxide emission, either for the existing ethanol plants or those to be built in the future.

Storage and transportation of gaseous fuels, e.g., hydrogen, are complicated and expensive practices because the system generally needs to be pressurized or super-cooled to −421° F. Therefore, there is a need to precondition these kinds of gaseous fuels and transform them into a form (such as, liquid at ambient temperature) that can be stored and transported more efficiently. Having an efficient on-site fuel precondition system that can transform hydrocarbon and carbon dioxide into liquid fuels is valuable because it reduces the cost to store and transport gaseous fuels and also controls the emission of hydrocarbon and carbon dioxide by transforming them into usable renewable energy.

BRIEF DESCRIPTION OF THE DRAWINGS

Like reference symbols and designations in the various drawings indicate like elements.

DETAILED DESCRIPTION

Techniques, methods, and systems are disclosed for preparing a renewable liquid fuel from hydrocarbon and carbon dioxide generated from anaerobic digestion of organic substances or from industrial emissions.

In one aspect, a method for preparing a liquid fuel can include: supplying hydrocarbon and carbon dioxide to a heated area of a reaction chamber in controlled volumes, forming carbon monoxide and hydrogen by energy provided by the heated area, transporting carbon monoxide, hydrogen, and additional hydrogen to a reactor in controlled volumes, forming the liquid fuel in the reactor by controlling the pressure in the reactor in order to achieve a predetermined object. The method can also include storing the liquid fuel in a storage device. The method provides an efficient way to handle hydrocarbon and carbon dioxide on-site and transform them into liquid fuels.

In another aspect, a method for preparing a liquid fuel can include: supplying hydrocarbon and carbon dioxide to a heat-controlled area of a reaction chamber in controlled volumes, forming carbon monoxide and hydrogen by energy provided by the heated area, transporting carbon monoxide, a part of generated hydrogen, and additional hydrogen to an reactor in controlled volumes, forming the liquid fuel in the reactor by controlling the pressure in the reactor in order to achieve a predetermined object. Meanwhile, another part of generated hydrogen can be used to form, with nitrogen, ammonia. The method can include storing the liquid fuel with the ammonia in a storage device. Storing the liquid fuel and ammonia together is cost efficient because they do not interact with each other and they are easily separated. The method provides an efficient way to handle hydrocarbon and carbon dioxide and transform them into liquid fuels on-site.

According to aspects of the disclosure, implementations of the methods above can optionally include one or more of the following features. For example, the predetermined objects can be decided according to a user's need. Predetermined objects can include: maximum liquid fuel outputs, energy efficiency (namely, the least energy input), or the longest life durations of catalysts. The pressure in the reactor can be controlled by adjusting volumes of input and output gases. The hydrocarbon and carbon dioxide can be pre-heated by a heat exchanger (e.g., using a recycled heat). The heated area can be heated from solar energy or from combustion by a combustor. Oxygen and additional monoxide can be supplied to the combustor in order to adjust the volume of carbon dioxide or provide heat energy to the heated area. The additional hydrogen can be supplied cyclically to the reactor, in order to achieve the predetermined object. The liquid fuel can be stored with water, carbon donor (e.g., a compound that provides carbon in chemical reactions; the carbon donor can be either dissolved or colloidal), ammonia, or additives that improve energy density. The carbon dioxide can be supplied from emissions of ethanol production plants. The hydrocarbon can include methane and the liquid fuel can include methanol. The method can include using the recycled heat energy to transform the liquid fuel back to the gaseous form if required.

In yet another aspect, a system for preparing a liquid fuel can include: a reaction chamber with a heated area, a reactor, a regulating device, and a storage device. The heated area receives hydrocarbon and carbon dioxide in controlled volumes, and provides energy to form carbon monoxide and hydrogen. The reactor receives carbon monoxide, generated hydrogen, and additional hydrogen in controlled volumes. The regulating device regulates the pressure in the reactor by adjusting all the controlled volumes and achieves a predetermined object. Then the reactor forms the liquid fuel according to the predetermined object. The storage device can be used to store the generated liquid fuel.

The subject matter described in this specification potentially can provide one or more of the following advantages. For example, the described techniques, methods, and systems can be used to avoid the high costs of compressing or cryogenically freezing gaseous fuels, such as hydrogen. In addition, the liquid fuels prepared and stored in the present invention can be easily accessible for various kinds of users. The described techniques can also be used to reduce the carbon dioxide generated by industries, such as ethanol plants.

Exemplary Method and System

Techniques, methods and systems are disclosed for preparation liquid fuels from hydrogen, selected hydrocarbons and carbon dioxide generated either from anaerobic digestion of organic substances or from emission from industrial activities (such as, ethanol production). More particularly, methods and systems for on-site preconditioning of hydrocarbon and carbon dioxide into usable liquid fuels are disclosed.

Figure 1:
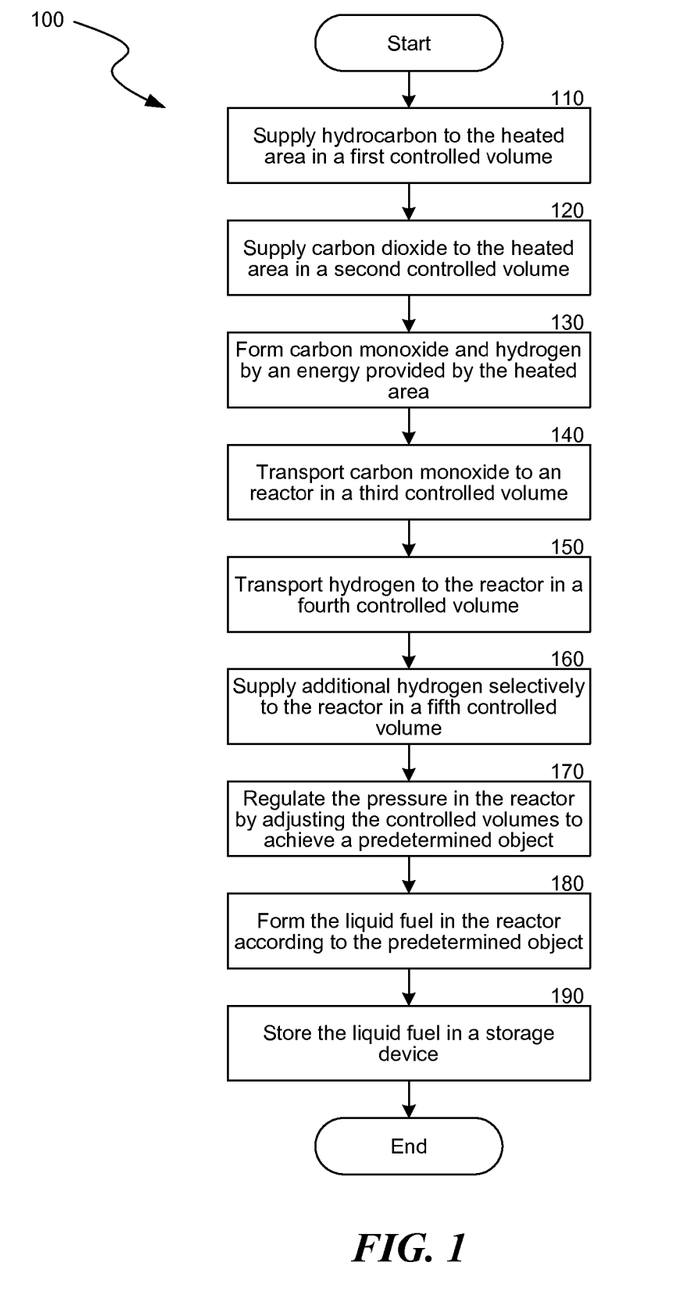
FIG. 1 is a process flow diagram, depicting an exemplary method for preparing a renewable liquid fuel of the present invention.

FIG. 1 is a process flow diagram, depicting an exemplary method for preparing a renewable liquid fuel of the present invention. As shown in FIG. 1, the method 100 starts at block 110 by supplying hydrocarbon to a heated area of a reaction chamber in a first controlled volume. Hydrocarbon can be from anaerobic digestion of organic substances (e.g., Equation 1 below) or from other emission sources. In some embodiments, hydrocarbon and carbon dioxide can be preheated by a heat exchanger that recycles the heat from the reaction chamber. The reaction chamber can be any types of device that defines a specific space within which chemical reactions can take place. The heated area can be an area that receives heat from other sources. In some embodiments, the heated area can be a reaction zone. In other embodiments, the heated area can be a porous tube where various catalysts can be placed. In some embodiments, the catalysts used in the heated area include nickel (around 20-30%) presented by alumina substrate (e.g., $Al_2O_3$).

The method continues at block 120 by supplying the carbon dioxide to the heated area of the reaction chamber in a second controlled volume. Carbon dioxide can be from anaerobic digestion of organic substances (e.g., Equation 1 below) or from other industrial emissions such as ethanol production plants. The supplied volumes of hydrocarbon and carbon dioxide can be controlled by any means that can control gas flows, such as a valve or other flow regulating devices. The volume control can be done manually by experienced operators, or automatically by a computer-monitored system.

$$C_xH_yO_z \rightarrow CH_4+CO_2 \qquad \text{Equation 1}$$

The method 100 continues at block 130 by forming carbon monoxide and hydrogen from hydrocarbon and carbon dioxide by energy provided by the heated area. The equation is shown as Equation 2 below. In some embodiments, the heat provided by the heated area can be from solar energy. In some embodiments, a light collection device can reflect and focus sunshine to heat up the heated area directly. The solar energy can be received, converted into different form of energy (such as, electricity), and then provides heat energy to the heated area. In other embodiments, the heated area can also be heated by an outflow of a combustor. In some embodiments, the combustor can selectively provide additional carbon dioxide to the heated area when necessary. For example, providing additional carbon dioxide to maintain the reaction rate when original carbon dioxide supply accidentally discontinues. In some embodiments, oxygen and additional carbon monoxide can be supplied to the combustor to generate heat and/or necessary carbon dioxide, as shown in Equation 3 below.

$$CO_2+CH_4+HEAT \rightarrow 2CO+2H_2 \qquad \text{Equation 2}$$

$$2CO+O_2 \rightarrow 2CO_2 \qquad \text{Equation 3}$$

After carbon monoxide and hydrogen are formed, the method 100 continues at block 140 and block 150 by transporting carbon monoxide and hydrogen to a reactor in a third controlled volume and a fourth controlled volume, respectively. The volumes of carbon monoxide and hydrogen can be controlled by any means that can control gas flows, such as a valve or other flow regulating devices. The volume control can be done manually by experienced operators, or automatically by a computer-monitored system. The chemical reaction to be performed in the reactor, as shown in Equations 4 and 5 below, prefers elevated pressure, and the reactor can be any suitable device that can sustain necessary reaction pressure and related conditions.

$$CO+H_2 \rightarrow CH_3OH \qquad \text{Equation 4}$$

$$CO2+3H_2 \rightarrow CH_3OH+H_2O \qquad \text{Equation 5}$$

The method 100 continues at block 160 by supplying additional hydrogen selectively to the reactor in a fifth controlled volume. According to alternative aspects off the disclosure, the additional hydrogen is not generated from the heated area, and can be produced by electrolysis and/or from chemical reaction outside the reaction chamber. One example is shown in Equation 6 below. The additional hydrogen can be supplied selectively according to the situation (e.g., pressure) in the reactor. In some embodiments, additional hydrogen can be pressurized and supplied to the reactor cyclically. The cyclic pressurization enables adequate dwell time of reactants in the reactor at favorable pressurization conditions, and thus provides favorable disturbance of the reactants, making reactant contacts with catalysts more efficiently. In some embodiments, the catalysts used in the reactor can include copper (Cu), zinc (Zn), aluminum (Al) or alumina ($Al_2O_3$). The volume of additional hydrogen can be controlled by any means that can control gas flows, such as a valve or other flow regulating devices.

The method 100 continues at block 170 by regulating the pressure in the reactor by adjusting controlled volumes to achieve a predetermined object and at block 180 by forming the liquid fuel according to the predetermined object. All the controlled volumes mentioned (e.g., volumes of hydrocarbon, carbon dioxide, additional carbon dioxide, oxygen, carbon monoxide, additional carbon monoxide, generated hydrogen, and additional hydrogen) can be adjusted to optimize the reaction condition, in order to achieve the predetermined object. The volumes can be controlled by any means that can control gas flows, such as a valve or other flow regulating devices. The volume control can be done manually by experienced operators, or automatically by a computer-monitored system. The predetermined object can include: maximize the liquid fuel production (as described at block 180 below), minimize the total energy consumption, or have the longest use duration of catalysts in the reaction chamber. Based on the predetermined object chosen, the liquid fuel can be formed from hydrocarbon and carbon dioxide. In some embodiments, the hydrocarbon can be methane and the liquid fuel can be methanol. Exemplary equations of the liquid fuel formation are shown in Equations 4 and 5 above.

The method 100 continues at block 190 by storing the liquid fuel in a storage device. In some embodiments, the liquid fuel from the reactor can pass through a heat exchanger before entering into the storage device. In some embodiments, the liquid fuel can be stored with water, carbon donor (e.g., a compound that provides carbon in chemical reactions; the carbon donor can be either dissolved or colloidal), ammonia, or additives that can be used to improve energy density of the liquid fuel, such as urea or nitrogenous compounds. The liquid fuel can be stored in different types depending on user preference. In some embodiments, the liquid fuel can be transformed into a gaseous form by heat energy recycled from the reaction chamber.

Figure 2:
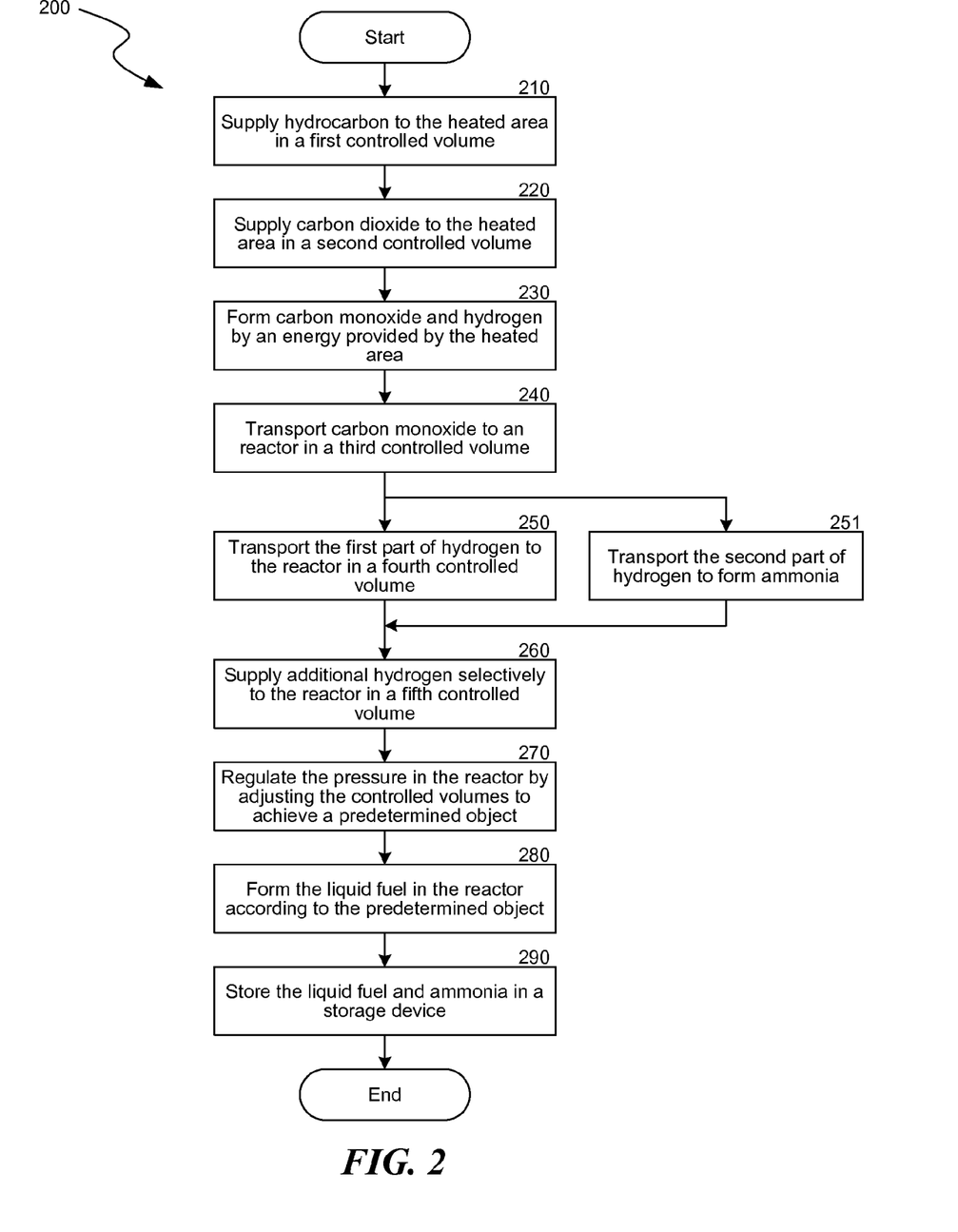
FIG. 2 is a process flow diagram, depicting another exemplary method for preparing a renewable liquid fuel of the present invention.

FIG. 2 is a process flow diagram, depicting another exemplary method for preparing a renewable liquid fuel of the present invention. As shown in FIG. 2, the method 200 starts at block 210 by supplying hydrocarbon to a heated area of a reaction chamber in a first controlled volume. Hydrocarbon can be from anaerobic digestion of organic substances (e.g., Equation 1 above) or from other emission sources. In some embodiments, hydrocarbon and carbon dioxide can be preheated by a heat exchanger that recycles the heat from the reaction chamber. The reaction chamber can be any types of device that defines a specific space within which chemical reactions can take place. The heated area can be an area that receives heat from other sources. In some embodiments, the heat area can be a reaction zone. In other embodiments, the heated area can be a porous tube that various catalysts can be placed. In some embodiments, the catalysts used in the heated area include nickel (around 20-30%) presented by alumina substrate (e.g., $Al_2O_3$).

The method 200 continues at block 220 by supplying carbon dioxide to the heated area of the reaction chamber in a second controlled volume. Carbon dioxide can be from anaerobic digestion of organic substances (e.g., Equation 1 above) or from other industrial emissions such as ethanol production plants. The supplied volumes of hydrocarbon and carbon dioxide can be controlled by any means that can control gas flows, such as a valve or other flow regulating devices. The volume control can be done manually by experienced operators, or automatically by a computer-monitored system.

The method 200 continues at block 230 by forming carbon monoxide and hydrogen from hydrocarbon and carbon dioxide by energy provided by the heated area. The equation is shown as Equation 2 above. In some embodiments, the heat provided by the heated area can be from solar energy. In some embodiments, a light collection device can reflect and focus sunshine to heat up the heated area directly. In other embodiments, the solar energy can be received, converted into different form of energy (such as, electricity), and then provides heat energy to the heated area. In other embodiments, the heated area can be heated by the outflow of a combustor. In some embodiments, the combustor can selectively provide additional carbon dioxide to the heated area when necessary. For example, providing additional carbon dioxide to maintain the reaction rate when original carbon dioxide supply accidentally discontinues. In some embodiments, oxygen and additional carbon monoxide can be supplied to the combustor to generate necessary carbon dioxide, as shown in Equation 3 above.

After carbon monoxide and hydrogen are formed, the method 200 continues at block 240 and block 250 by transporting carbon monoxide and a first part of hydrogen to a reactor in a third controlled volume and a fourth controlled volume, respectively. The volumes of carbon monoxide and the first part of hydrogen can be controlled by any means that can control gas flows, such as a valve or other flow regulating devices. The volume control can be done manually by experienced operators, or automatically by a computer-monitored system. The chemical reaction to be performed in the reactor, as shown in Equation 4 above, prefers elevated pressure, and the reactor can be any suitable devices that can sustain necessary pressure.

Meanwhile, the method 200 continues at block 251 by transporting a second part of the hydrogen to form ammonia with nitrogen, as shown in Equation 7 below. The nitrogen necessary to feed the reaction can be supplied from the atmosphere or other sources. The generated ammonia can be feed stocks of hydrogen and nitrogen and supply them to further uses when necessary. The generated ammonia can be separated by selective membranes or pressurized by temperature and/or charge swing processes that utilize graphenme storage media. The generated ammonia can be stored with the liquid fuel to be produced in a storage device (see block 290 below).

The method 200 continues at block 260 by supplying additional hydrogen selectively to the reactor in a fifth controlled volume. The additional hydrogen can be produced by electrolysis, from the generated ammonia as discussed at block 251 above, and/or from chemical reaction outside the reaction chamber (e.g., Equation 5 above). The additional hydrogen can be supplied selectively according to the situation (e.g., pressure) in the reactor. In some embodiments, the additional hydrogen can be pressurized and supplied to the reactor cyclically. The cyclic pressurization enables adequate dwell time of reactants in the reactor at favorable pressurization conditions, and thus provides favorable disturbance of the reactants, making reactants contacts with catalysts more efficiently. some embodiments, the catalysts used in the reactor can include copper (Cu), zinc (Zn) or alumni (Al). The volume of additional hydrogen can be controlled by any means that can control gas flows, such as a valve or other flow regulating devices.

The method 200 continues at block 270 by regulating the pressure in the reactor by adjusting controlled volumes to achieve a predetermined object and at block 280 by forming the liquid fuel according to the predetermined object. All the controlled volumes mentioned (e.g., volumes of hydrocarbon, carbon dioxide, additional carbon dioxide, oxygen, carbon monoxide, additional carbon monoxide, generated hydrogen, and additional hydrogen) can be adjusted to optimize the reaction condition, in order to achieve the predetermined object. The volumes can be controlled by any means that can control gas flows, such as a valve or other flow regulating devices. The volume control can be done manually by experienced operators, or automatically by a computer-monitored system. The predetermined object can include: maximize the liquid fuel production (as described at block 280 below), minimize the total energy consumption, or have the longest use duration of catalysts used in the reaction chamber. Based on the predetermined object chosen, the liquid fuel can be formed from hydrocarbon and carbon dioxide. In some embodiments, the hydrocarbon can be methane and the liquid fuel can be methanol. An exemplary equation of the liquid fuel formation is shown in Equation 4 above.

The method 200 continues at block 290 by storing the liquid fuel and the ammonia in a storage device. In some embodiments, the liquid fuel from the reactor can pass through a heat exchanger before entering into the storage device. In some embodiments, the liquid fuel can also be stored with water, carbon donor, or additives that can be used to improve energy density of the liquid fuel, such as urea or nitrogenous compounds. The liquid fuel can be stored in different types depending on user preference. In some embodiments, the liquid fuel can be transformed into a gaseous form by heat energy recycled from the reaction chamber.

Figure 3:
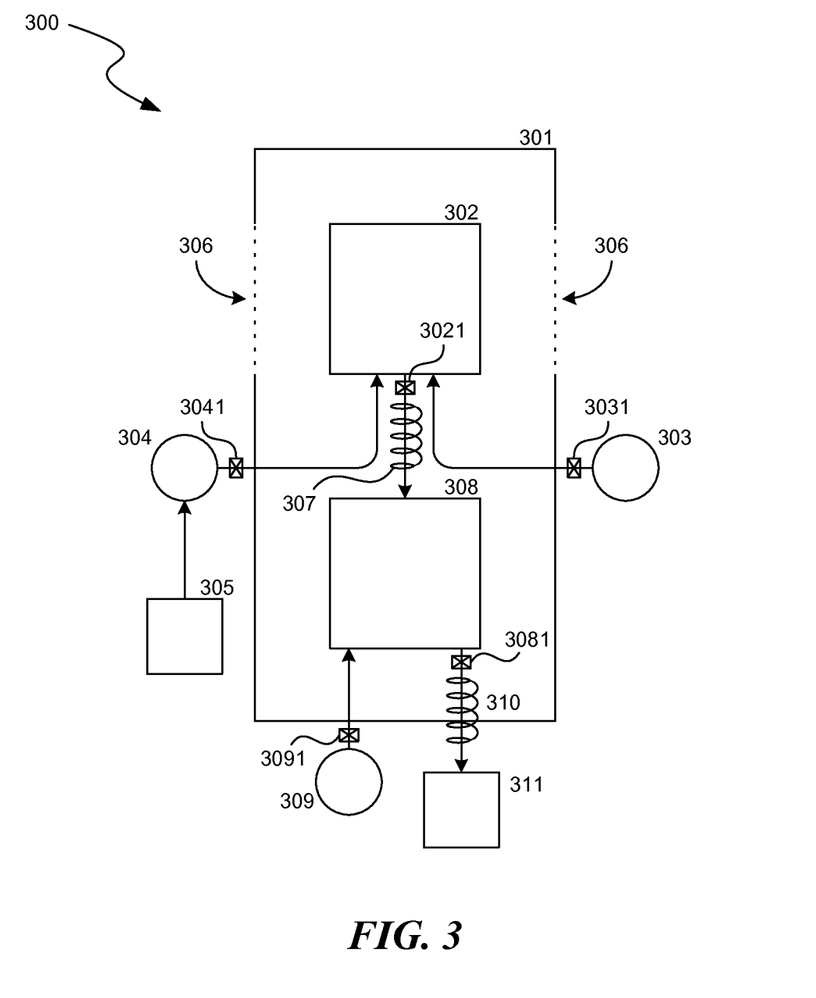
FIG. 3 is a schematic diagram, depicting an exemplary system for preparing a renewable liquid fuel of the present invention.

FIG. 3 is a schematic diagram, depicting an exemplary system 300 for preparing a renewable liquid fuel of the present invention. The system 300 includes a reaction chamber 301, a heated area 302, a solar window 306, a reactor 308 and a storage device 311. The system 300 includes a hydrocarbon source 303 to supply hydrocarbon to the heated area 302, and a carbon dioxide source 304 to supply carbon dioxide to the heated area 302. The hydrocarbon source 303 can receive hydrocarbon from anaerobic digestion of organic substances (e.g., Equation 1 above) or from other emission sources. The valve 3031 controls the volume of carbon dioxide supplied to the heated area 302. The carbon dioxide source 304 can receive carbon dioxide from anaerobic digestion of organic substances (e.g., Equation 1 above) or from other industrial emissions such as ethanol production plants 305. The valve 3041 controls the volume supplied to the heated area 302.

After receiving hydrocarbon and carbon dioxide, the heated area 302 can provide necessary energy to form carbon monoxide and hydrogen as described in Equation 2 above. In some embodiments, the heat provided by the heated area 302 can be from solar energy through the solar windows 306. In some embodiments, a light collection device (not shown) can reflect and focus sunshine through the solar window 306 to heat up the heated area 302. In other embodiments, the solar energy can be received and converted into different form of energy (such as, electricity), and then provide heat energy to the heated area 302. The solar windows 306 can be closed when the heated area 302 has sufficient heat energy to form monoxide and hydrogen. In some embodiments, the catalysts used in the heated area 302 include nickel (around 20-30%) presented by alumina substrate (e.g., $Al_2O_3$).

As shown in FIG. 3, carbon monoxide and hydrogen generated in heated area 302 can be transported to a reactor 308 through a heat exchanger 307. For, example, the heat exchanger 307 can take the heat from generated carbon monoxide and hydrogen (e.g., while transporting to the reactor 308) to pre-heat the hydrocarbon from the hydrocarbon source 303 and the carbon dioxide from the carbon dioxide source 304. The valve 3021 can control the volumes of carbon monoxide and hydrogen transported to the reactor 308.

As shown in FIG. 3, the additional hydrogen source 309 can selectively provide additional hydrogen to the reactor 308. The valve 3091 can control the volume of additional hydrogen transported to the reactor 308. The additional hydrogen can be produced by electrolysis and/or from chemical reaction outside the reaction chamber (e.g., as shown in Equation 5 above). The additional hydrogen can be supplied selectively according to the situation (e.g., pressure) in the reactor. In some embodiments, the additional hydrogen can be pressurized and supplied to the reactor cyclically. The cyclic pressurization enables adequate dwell time of reactants in the reactor 308 at favorable pressurization conditions, and thus provides favorable disturbance of the reactants, making reactant contacts with catalysts more efficiently.

After receiving carbon monoxide and hydrogen, the reactor 308 can form the liquid fuel from according to a predetermined object. The predetermined object can include: maximize the liquid fuel production, minimize the total energy consumption, or longest use duration of catalysts used in the reaction chamber. Based on the predetermined object chosen, the liquid fuel can be formed from hydrocarbon and carbon dioxide. In some embodiments, the catalysts used in the reactor 308 can include copper (Cu), zinc (Zn) or alumni (Al). In some embodiments, the hydrocarbon can be methane and the liquid fuel can be methanol. An exemplary equation of the liquid fuel formation is shown in Equation 4 above.

A regulating device (not shown) can regulate the pressure in the reactor 308 by adjusting all controlled volumes (e.g., through various valves 3031, 3041, 3021 and 3081), in order to achieve the predetermined object. In some embodiments, the regulating device can be a computer-operated device equipped with suitable sensors that can monitor the situation of the reaction chamber 301, the heated area 302, the reactor 308 and the storage device 311. In other embodiments, the regulating device can be manually operated to achieve the predetermined object.

As shown in FIG. 3, the reactor 308 can transport the liquid fuel, through a valve 3081 and a heat exchanger 310, to a storage device 311. The valve 3081 can control the flow of the liquid fuel transported to the storage device 311. The heat exchanger 310 can recycle heat energy from the liquid fuel for further use. The storage device 311 can store water, carbon donor, ammonia, or additives that can be used to improve energy density of the liquid fuel, such as urea or nitrogenous compounds. The liquid fuel can be stored in different types depending on user preference. In some embodiments, the liquid fuel can be transformed into a gaseous form by heat energy recycled from the system 300.

Figure 4:
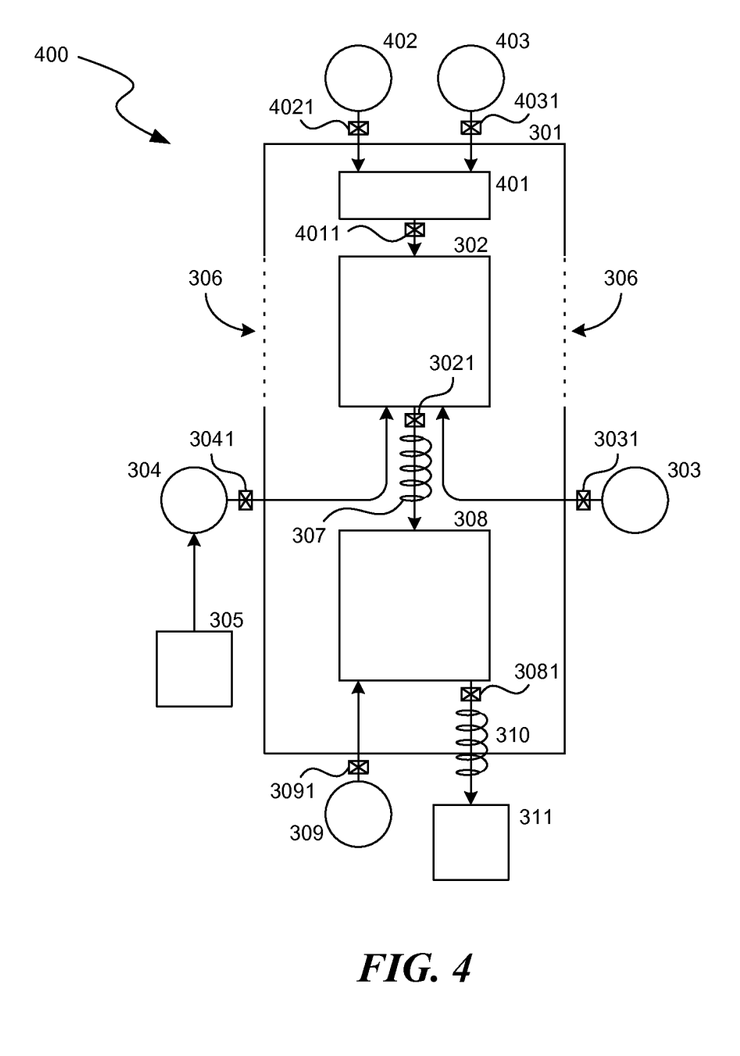
FIG. 4 is a schematic diagram, depicting another exemplary system for preparing a renewable liquid fuel of the present invention.

FIG. 4 is a schematic diagram, depicting yet another exemplary system 400 for preparing a renewable liquid fuel of the present invention. The system 400 includes a reaction chamber 301, a heated area 302, a solar window 306, a reactor 308, a combustor 401, and a storage device 311. The system 300 includes a hydrocarbon source 303 to supply hydrocarbon to the heated area 302, and a carbon dioxide source 304 to supply carbon dioxide to the heated area 302. The hydrocarbon source 303 can receive hydrocarbon from anaerobic digestion of organic substances (e.g., Equation 1 above) or from other emission sources. The valve 3031 controls the volume of hydrocarbon supplied to the heated area 302. The carbon dioxide source 304 can receive carbon dioxide from anaerobic digestion of organic substances (e.g., Equation 1 above) or from other industrial emissions such as an ethanol plant 305. The valve 3041 controls the volume of carbon dioxide supplied to the heated area 302.

After receiving hydrocarbon and carbon dioxide, the heated area 302 can provide necessary energy to form carbon monoxide and hydrogen as described in Equation 2 and related descriptions for the embodiments of FIG. 3 above. In some embodiments, the heat provided by the heated area 302 can be from solar energy as described in the related descriptions for the embodiments of FIG. 3 above. In FIG. 4, the combustor 401 can be used to provide heat energy to the heated area 302 when other sources (e.g., solar energy from the solar window 306) are not available (e.g., during the night time). In addition, the combustor 401 can provide additional carbon dioxide to the heated area 302 when necessary. The valve 4011 can control the volume of carbon dioxide supplied to the combustor 401. For example, supply from the carbon dioxide source 304 may be interrupted accidentally. In some embodiments, the oxygen source 402 can supply oxygen to the combustor 401 to facilitate the combustion. The valve 4021 can control the volume of the oxygen supplied to the combustor 401. In some embodiments, the carbon monoxide source 403 can supply carbon monoxide to the combustor 401 to facilitate the generation of additional carbon dioxide as shown in Equation 3 above. The valve 4031 can control the volume of the oxygen supplied to the combustor 401. In some embodiments, the catalysts used in the heated area 302 include nickel (around 20-30%) presented by alumina substrate (e.g., $Al_2O_3$).

As shown in FIG. 4, carbon monoxide and hydrogen generated in heated area 302 can be transported to a reactor 308 through a heat exchanger 307. The heat exchanger 307 can take the heat from carbon monoxide and hydrogen (e.g., while transporting to the reactor 308) to pre-heat the hydrocarbon from the hydrocarbon source 303 and carbon dioxide from the carbon dioxide source 304. The valve 3021 can control the volumes of carbon monoxide and hydrogen transported to the reactor 308. As shown in FIG. 4, the additional hydrogen source 309 can selectively provide additional hydrogen to the reactor 308. The valve 3091 can control the volume of hydrogen transported to the reactor 308. The additional hydrogen can be produced by electrolysis and/or from chemical reaction outside the reaction chamber (e.g., Equation 5 above). The additional hydrogen can be supplied selectively according to the situation (e.g., pressure) in the reactor. In some embodiments, the additional hydrogen can be pressurized and supplied to the reactor cyclically. The cyclic pressurization enables adequate dwell time of reactants in the reactor 308 at favorable pressurization conditions, and thus provides favorable disturbance of the reactants, making reactant contacts with catalysts more efficiently.

After receiving carbon monoxide and hydrogen, the reactor 308 can form the liquid fuel from according to a predetermined object. The predetermined object can include: maximize the liquid fuel production, minimize the total energy consumption, or longest use duration of catalysts used in the reaction chamber. Based on the predetermined object chosen, the liquid fuel can be formed from hydrocarbon and carbon dioxide. In some embodiments, the catalysts used in the reactor 308 can include copper (Cu), zinc (Zn) or alumni (Al). In some embodiments, the hydrocarbon can be methane and the liquid fuel can be methanol. An exemplary equation of the liquid fuel formation is shown in Equation 4 above.

A regulating device (not shown) can regulate the pressure in the reactor 308 by adjusting all controlled volumes (e.g., through various valves 3031, 3041, 3021 and 3081), in order to achieve the predetermined object. In some embodiments, the regulating device can be a computer-operated device equipped with suitable sensors that monitor the situation of the reaction chamber 301, the heated area 302, the reactor 308, and the storage device 311. In other embodiments, the regulating device can be manually operated to achieve the predetermined object.

As shown in FIG. 4, the reactor 308 can transport the liquid fuel, through a valve 3081 and a heat exchanger 310, to a storage device 311. The valve 3081 can control the flow of the liquid fuel transported to the storage device 311. The heat exchanger 310 can recycle heat energy from the liquid fuel for further use. The storage device 311 can include water, carbon donor, ammonia, or additives that can be used to improve energy density of the liquid fuel, such as urea or nitrogenous compounds. The liquid fuel can be stored in different types depending on user preference. In some embodiments, the liquid fuel can be transformed into a gaseous form by heat energy recycled from the system 400.

Figure 5:
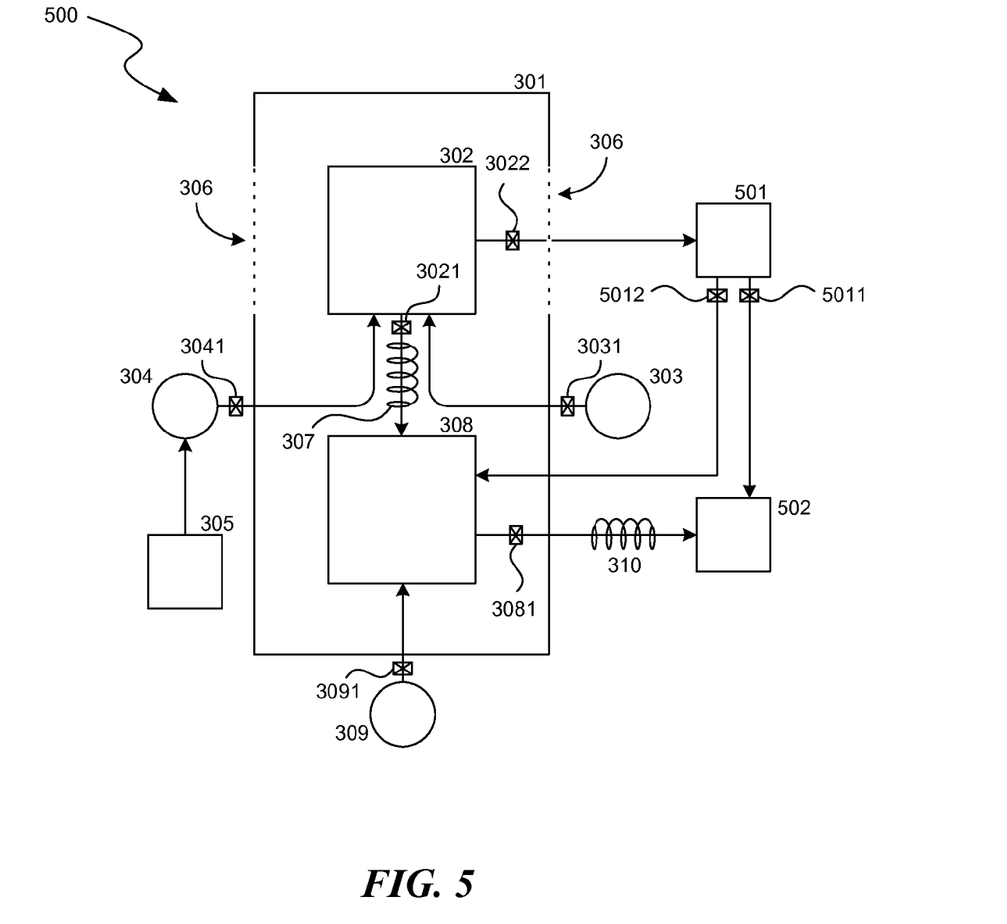
FIG. 5 is a schematic diagram, depicting yet another exemplary system for preparing a renewable liquid fuel of the present invention.

FIG. 5 is a schematic diagram, depicting yet another exemplary system 500 for preparing a renewable liquid fuel of the present invention. The system 500 includes a reaction chamber 301, a heated area 302, a solar window 306, a reactor 308, an ammonia reactor 501, and a storage device 502. The system 500 includes a hydrocarbon source 303 to supply hydrocarbon to the heated area 302, and a carbon dioxide source 304 to supply carbon dioxide to the heated area 302. The hydrocarbon source 303 can receive hydrocarbon from anaerobic digestion of organic substances (e.g., Equation 1 above) or from other emission sources. The valve 3031 controls the volume of carbon dioxide supplied to the heated area 302. The carbon dioxide source 304 can receive carbon dioxide from anaerobic digestion of organic substances (e.g., Equation 1 above) or from other industrial emissions such as an ethanol plant 305. The valve 3041 controls the volume supplied to the heated area 302.

After receiving hydrocarbon and carbon dioxide, the heated area 302 can provide necessary energy to form carbon monoxide and hydrogen as described in Equation 2 above. In some embodiments, the heat provided by the heated area 302 can be from solar energy through the solar window 306. In some embodiments, a light collection device (not shown) can reflect and focus sunshine through the solar window 306 to heat up the heated area 302. In other embodiments, the solar energy can be received, converted into different form of energy (such as, electricity), and then heat up the heated area 302. The solar window 306 can be closed when the heated area 302 has sufficient heat to form monoxide and hydrogen. In some embodiments, the heated area 302 can receive heat energy from a combustor 401, as described above. In some embodiments, the catalysts used in the heated area 302 include nickel (around 20-30%) presented by alumina substrate (e.g., $Al_2O_3$).

As shown in FIG. 5, carbon monoxide and the first part of the generated hydrogen in heated area 302 can be transported to a reactor 308 through a heat exchanger 307. The heat exchanger 307 can take the heat from carbon monoxide and the first part of the generated hydrogen to pre-heat the hydrocarbon from the hydrocarbon source 303 and carbon dioxide from the carbon dioxide source 304. The valve 3021 can control the volumes of carbon monoxide and hydrogen transported to the reactor 308.

As shown in FIG. 5, the second part of the generated hydrogen can be transported to the ammonia reactor 501 to form ammonia with nitrogen, as described in Equation 6 above. The valve 3022 can control the volume of hydrogen transported to the ammonia reactor 501. The volumes of the first part and the second part of the generated hydrogen can be determined by the predetermined objected described above. The nitrogen necessary to the reaction can be supplied from the atmosphere or other sources. The generated ammonia can be feed stocks of hydrogen and nitrogen when necessary. The generated ammonia can be separated into hydrogen and nitrogen by selective membranes or pressurized by temperature and/or charge swing processes that utilize graphene storage media. The valve 5011 can control the volume of ammonia transported to the storage device 502 and the valve 5012 can control the volume of additional hydrogen separated from ammonia to the reactor 308. The ammonia can be stored with the liquid fuel to be produced in the storage device 502.

As shown in FIG. 5, the additional hydrogen source 309 can selectively provide additional hydrogen to the reactor 308. The valve 3091 can control the volume of hydrogen transported to the reactor 308. The additional hydrogen can be produced by electrolysis, separation from ammonia generated in the ammonia reactor 501, and/or from chemical reaction outside the reaction chamber (e.g., Equation 5 above). The additional hydrogen can be supplied selectively according to the situation (e.g., pressure) in the reactor. In some embodiments, the additional hydrogen can be pressurized and supplied to the reactor cyclically. The cyclic pressurization enables adequate dwell time of reactants in the reactor 308 at favorable pressurization conditions, and thus provides favorable disturbance of the reactants, making reactant contacts with catalysts more efficiently.

After receiving carbon monoxide and the first part of the generated hydrogen, the reactor 308 can form the liquid fuel from according to a predetermined object. The predetermined object can include: maximize the liquid fuel production, minimize the total energy consumption, or longest use duration of catalysts used in the reaction chamber. Based on the predetermined object chosen, the liquid fuel can be formed from hydrocarbon and carbon dioxide. In some embodiments, the catalysts used in the reactor 308 can include copper (Cu), zinc (Zn) or alumni (Al). In some embodiments, the hydrocarbon can be methane and the liquid fuel can be methanol. An exemplary equation of the liquid fuel formation is shown in Equation 4 above.

A regulating device (not shown) can regulate the pressure in the reactor 308 by adjusting all controlled volumes (e.g., through various valves 3031, 3041, 3021, 3081, 3091, 3022, 5011, and 5012), in order to achieve the predetermined object. In some embodiments, the regulating device can be a computer-operated device equipped with suitable sensors that monitor the situation of the reaction chamber 301, the heated area 302, the reactor 308, the ammonia reactor 501, and the storage device 502. In other embodiments, the regulating device can be manually operated to achieve the predetermined object.

As shown in FIG. 5, the reactor 308 can transport the liquid fuel, through a valve 3081 and a heat exchanger 310, to a storage device 502. The valve 3081 can control the flow of the liquid fuel transported to the storage device 502. The heat exchanger 310 can recycle heat energy from the liquid fuel for further use. The heat exchanger 310 can also adjust the temperature of the additional hydrogen supplied from the ammonia reactor 501 before it enters the reactor 308.

In addition to the liquid fuel and ammonia, the storage device 502 can also store water, carbon donor, or additives that can be used to improve energy density of the liquid fuel, such as urea or nitrogenous compounds. The liquid fuel can be stored in different types depending on users' preference. In some embodiments, the liquid fuel can be transformed into a gaseous form by heat energy recycled from the system 500.

An application of a liquid fuel such as CH3OH or NH3 in a fuel cell or heat engine such as a gas turbine, rotary combustion or positive displacement piston engine provides for commensurate delivery of carbon dioxide and/or nitrogen and/or thermal energy. This enables economic development of processes including enhanced photosynthesis of crops in greenhouse and hydroponic systems. Deliveries of such nitrogen similarly enables greatly improved utilization of nitrogen in processes such as furnace conversion of powder molded silicon articles to silicon nitride ceramics.

The liquid fluid described in this invention can be transformed into polymers for further industrial uses. For example, in some embodiments, the liquid fuel can be methanol and it can be further converted into ethylene or propylene, and then aggregated as polymers, such as polyethylene or polypropylene.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

To the extent not previously incorporated herein by reference, the present application incorporates by reference in their entirety the subject matter of each of the following materials: application Ser. No. 13/027,208, filed on Feb. 14, 2011 and titled CHEMICAL PROCESSES AND REACTORS FOR EFFICIENTLY PRODUCING HYDROGEN FUELS AND STRUCTURAL MATERIALS, AND ASSOCIATED SYSTEMS AND METHODS; application Ser. No. 13/026,996, filed on Feb. 14, 2011 and titled REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS; application Ser. No. 13/027,015, filed on Feb. 14, 2011 and titled CHEMICAL REACTORS WITH RE-RADIATING SURFACES AND ASSOCIATED SYSTEMS AND METHODS; application Ser. No. 13/027,244, filed on Feb. 14, 2011 and titled THERMAL TRANSFER DEVICE AND ASSOCIATED SYSTEMS AND METHODS; application Ser. No. 13/026,990, filed on Feb. 14, 2011 and titled CHEMICAL REACTORS WITH ANNULARLY POSITIONED DELIVERY AND REMOVAL DEVICES, AND ASSOCIATED SYSTEMS AND METHODS; application Ser. No. 13/027,181, filed on Feb. 14, 2011 and titled REACTORS FOR CONDUCTING THERMOCHEMICAL PROCESSES WITH SOLAR HEAT INPUT, AND ASSOCIATED SYSTEMS AND METHODS; application Ser. No. 13/027,215, filed on Feb. 14, 2011 and titled INDUCTION FOR THERMOCHEMICAL PROCESS, AND ASSOCIATED SYSTEMS AND METHODS; application Ser. No. 13/027,198, filed on Feb. 14, 2011 and titled COUPLED THERMOCHEMICAL REACTORS AND ENGINES, AND ASSOCIATED SYSTEMS AND METHODS; U.S. Patent Application No. 61/385,508, filed on Sep. 22, 2010 and titled REDUCING AND HARVESTING DRAG ENERGY ON MOBILE ENGINES USING THERMAL CHEMICAL REGENERATION; application Ser. No. 13/027,060, filed on Feb. 14, 2011 and titled REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS; U.S. Patent Application No. 61/237,419, filed on Aug. 27, 2009 and titled CARBON SEQUESTRATION; application Ser. No. 13/027,068, filed on Feb. 14, 2011 and titled SYSTEM FOR PROCESSING BIOMASS INTO HYDROCARBONS, ALCOHOL VAPORS, HYDROGEN, CARBON, ETC.; application Ser. No. 13/027,196, filed on Feb. 14, 2011 and titled CARBON RECYCLING AND REINVESTMENT USING THERMOCHEMICAL REGENERATION; application Ser. No. 13/027,195, filed on Feb. 14, 2011 and titled OXYGENATED FUEL; U.S. Patent Application No. 61/237,425, filed on Aug. 27, 2009 and titled OXYGENATED FUEL PRODUCTION; application Ser. No. 13/027,197, filed on Feb. 14, 2011 and titled MULTI-PURPOSE RENEWABLE FUEL FOR ISOLATING CONTAMINANTS AND STORING ENERGY; and application Ser. No. 13/027,185, filed on Feb. 14, 2011 and titled ENGINEERED FUEL STORAGE, RESPECIATION AND TRANSPORT.

I claim:

1. A method for preparing a liquid fuel, the method comprising:
supplying a first controlled volume of hydrocarbon to a heated area positioned within a reaction chamber, wherein the reaction chamber has a housing and the housing further has at least one solar window;
supplying a second controlled volume of carbon dioxide to the heated area;
at least partially opening or closing the solar window in response to a status of the heated area;
forming carbon monoxide and hydrogen from the hydrocarbon and the carbon dioxide at the heated area;
transporting a third controlled volume of the carbon monoxide to a reactor positioned within the reaction chamber;
transporting a fourth controlled volume of the hydrogen to the reactor;
selectively supplying a fifth controlled volume of additional hydrogen to the reactor;
adjusting the controlled volumes to regulate a pressure in the reactor so as to achieve a predetermined object; and
forming the liquid fuel from the hydrogen and the carbon monoxide in the reactor according to the predetermined object.

2. The method of claim 1, wherein the predetermined object includes at least one of a maximum production of the liquid fuel, a minimum energy input to the reaction chamber, and a longest use duration of a catalyst used in the reaction chamber.

3. The method of claim 1, wherein the pressure in the reactor is regulated by a valve located between the heated area and the reactor.

4. The method of claim 1, further comprising:
heating up the hydrocarbon and the carbon dioxide by a heat exchanger.

5. The method of claim 1, wherein the additional hydrogen is pressurized and supplied cyclically.

6. The method of claim 1, further comprising:
generating a sixth controlled volume of additional carbon dioxide by a combustor; and
heating the heated area by the combustor.

7. The method of claim 6, further comprising:
supplying a seventh controlled volume of oxygen to the combustor; and
supplying an eighth controlled volume of additional carbon monoxide to the combustor.

8. The method of claim 1, further comprising:
directly heating the heated area by solar energy.

9. The method of claim 1, wherein the hydrocarbon comprises methane, and wherein the liquid fuel comprises methanol.

10. The method of claim 1, further comprising:
transforming the liquid fuel into a gaseous form by recycled heat energy.

11. The method of claim 1, wherein the liquid fuel is stored with at least one of water, a carbon donor, ammonia, and an additive used to improve energy density.

12. The method of claim 1, wherein the carbon dioxide is supplied from an ethanol plant.

13. A method for preparing a liquid fuel, the method comprising:
supplying a first controlled volume of hydrocarbon to a heated area positioned within a reaction chamber, wherein the reaction chamber has a housing and the housing further has at least one solar window;
supplying a second controlled volume of carbon dioxide to the heated area;
at least partially opening or closing the solar window in response to a status of the heated area;
forming carbon monoxide and hydrogen from the hydrocarbon and the carbon dioxide by at the heated area;
transporting a third controlled volume of the carbon monoxide to a reactor positioned within the reaction chamber;
transporting a fourth controlled volume of a first part of the hydrogen to the reactor;
transporting a second part of the hydrogen to form ammonia;
selectively supplying a fifth controlled volume of additional hydrogen to the reactor;
adjusting the controlled volumes to regulate a pressure in the reactor so as to achieve a predetermined object;
forming the liquid fuel from the hydrogen and the carbon monoxide in the reactor; and
storing the liquid fuel and the ammonia in a storage device.

14. The method of claim 13, wherein the predetermined object includes at least one of a maximum production of the liquid fuel, a minimum energy input to the reaction chamber, and a longest use duration of a catalyst used in the reaction chamber.

15. The method of claim 13, wherein the pressure in the reactor is regulated by a valve located between the heated area and the reactor.

16. The method of claim 13, further comprising:
heating up the hydrocarbon and the carbon dioxide by a heat exchanger.

17. The method of claim 13, wherein the additional hydrogen is pressurized and supplied cyclically.

18. The method of claim 13, further comprising:
generating a sixth controlled volume of additional carbon dioxide by a combustor; and
heating the heated area by the combustor.

19. The method of claim 18, further comprising:
supplying a seventh controlled volume of oxygen to the combustor; and
supplying an eighth controlled volume of additional carbon monoxide to the combustor.

20. The method of claim 13, further comprising:
directly heating the heated area by solar energy.

21. The method of claim 13, wherein the hydrocarbon comprises methane, and wherein the liquid fuel comprises methanol.

22. The method of claim 13, further comprising:
transforming the liquid fuel into a gaseous form by recycled heat energy.

23. The method of claim 13, wherein the liquid fuel is stored with at least one of water, a carbon donor, and an additive used to improve energy density.

24. The method of claim 13, wherein the carbon dioxide is supplied from an ethanol plant.

* * * * *